United States Patent
Raoult et al.

(10) Patent No.: US 10,626,421 B2
(45) Date of Patent: Apr. 21, 2020

(54) USE OF URIC ACID FOR CULTURING BACTERIA SENSITIVE TO OXYGEN TENSION

(71) Applicants: FONDATION MEDITERRANEE INFECTION, Marseilles (FR); UNIVERSITE D'AIX MARSEILLE, Marseilles (FR); CENTRE NATIONAL DE LA RECHERCHE SCIENTIFIQUE (CNRS), Paris (FR); INSERM (INSTITUT NATIONAL DE LA SANTE ET DE LA RECHERCHE MEDICALE), Paris (FR)

(72) Inventors: Didier Raoult, Marseilles (FR); Saber Khelaifia, Marseilles (FR); Michel Drancourt, Marseilles (FR)

(73) Assignees: FONDATION MEDITERRANEE INFECTION FACULTÉ DE MÉDECINE, Marseilles (FR); UNIVERSITE D'AIX MARSEILLE, Marseilles (FR); CENTRE NATIONAL DE LA RECHERCHE SCIENTIFIQUE (CNRS), Paris (FR); INSERM (INSTITUT NATIONAL DE LA SANTE ET DE LA RECHERCHE MEDICALE), Paris (FR)

(*) Notice: Subject to any disclaimer, the term of this patent is extended or adjusted under 35 U.S.C. 154(b) by 390 days.

(21) Appl. No.: 15/304,887

(22) PCT Filed: Apr. 21, 2015

(86) PCT No.: PCT/FR2015/051082
§ 371 (c)(1),
(2) Date: Oct. 18, 2016

(87) PCT Pub. No.: WO2015/162377
PCT Pub. Date: Oct. 29, 2015

(65) Prior Publication Data
US 2017/0183620 A1 Jun. 29, 2017

(30) Foreign Application Priority Data

Apr. 23, 2014 (FR) .................................. 14 53652
Jun. 20, 2014 (FR) .................................. 14 55745
Sep. 15, 2014 (FR) .................................. 14 58622

(51) Int. Cl.
*C12N 1/20* (2006.01)
*C12P 5/02* (2006.01)
*C12P 39/00* (2006.01)
*C12N 1/38* (2006.01)

(52) U.S. Cl.
CPC ................ *C12P 5/023* (2013.01); *C12N 1/20* (2013.01); *C12N 1/38* (2013.01); *C12P 39/00* (2013.01); *Y02E 50/343* (2013.01)

(58) Field of Classification Search
None
See application file for complete search history.

(56) References Cited

FOREIGN PATENT DOCUMENTS

| WO | 2013/110891 A1 | 8/2013 |
|----|----------------|--------|
| WO | 2014/064359 A1 | 5/2014 |

OTHER PUBLICATIONS

Rouf et al. "Degradation of Uric Acid by Certain Aerobic Bacteria" Journal of Bacteriology, Sep. 1968, p. 617-622.*
Kole et al. "Protease production by Bacillus subtilis in oxygen-controlled, glucose fed-batch fermentations" Appl Microbiol Biotechnol (1988) 28:404-408.*
Chen et al. "Microbial fed-batch production of 1,3-propanediol by Klebsiella pneumoniae under micro-aerobic conditions" Appl Microbiol Biotechnol (2003) 63:143-146.*
International Search Report dated Jul. 21, 2015 for Application No. PCT/FR2015/051082.
La Scola, B., et al., "Aerobic culture of anaerobic bacteria using antioxidants: a preliminary report", Eur. J. Clin. Microbiol. Infect. Dis., vol. 33, No. 10, May 13, 2014, pp. 1781-1783.
Krieg, N. R., et al., "Microaerophily and Oxygen Toxicity", Ann. Rev. Microbiol., vol. 4, No. 1, Oct. 1, 1986, pp. 107-130.
Anonymous: "Uric Acid in Cell Culture", Jun. 4, 2013 (Jun. 4, 2013). XP055177496.
Wilkinson, S. P., et al., HucR, a Novel Uric Acid-responsive Member of the MarR Family of Transcriptional Regulators from *Deinococcus radiodurans*, The Journal of Biological Chemistry, vol. 279, No. 49, Dec. 3, 2004, pp. 51442-51450.

* cited by examiner

*Primary Examiner* — Thane Underdahl
(74) *Attorney, Agent, or Firm* — Ladas & Parry LLP; Malcolm J. MacDonald

(57) ABSTRACT

The present invention relates to a method for cultivating in vitro in an acellular culture medium, bacteria for which the growth is sensitive to oxygen content, said bacterium being selected from anaerobic bacteria and intracellular micro-aerophilic bacteria, characterized in that uric acid is added into said acellular culture medium, and said bacterium is cultivated in said culture medium in the presence of oxygen.

9 Claims, No Drawings

USE OF URIC ACID FOR CULTURING BACTERIA SENSITIVE TO OXYGEN TENSION

The present invention relates to the culture in an acellular medium of bacteria, the growth of which is sensitive to oxygen tension, notably bacteria which poorly tolerate high oxygen tensions and for which optimum growth of said bacterium requires an incubation atmosphere with a relatively reduced oxygen tension with respect to the oxygen tension of air or even strict anaerobic bacteria for which oxygen is toxic and which should be cultivated in total absence of oxygen or only tolerating low concentrations of oxygen.

Therefore among the bacteria sensitive to oxygen are distinguished:

- micro-aerophilic bacteria i.e. which are not able to be cultivated under an atmosphere comprising the ambient oxygen concentration which is of about 21%, notably between 1% and 20%, more commonly at about 2-2.5%, and
- strict anaerobic bacteria i.e. they are not capable of being cultivated in the presence of oxygen or in lower concentrations than the micro-aerophilic concentrations, notably strictly less than 1%, more commonly less than 0.1%, ideally 0%. In order to cultivate strict anaerobic bacteria, either they have to be cultivated in ovens not including any oxygen, or in tubes which have not been deoxygenated and which then only grow at the bottom of the tube.

From among strict anaerobic bacteria, are more particularly mentioned extracellular bacteria, i.e. bacteria which can only thrive outside cells.

More particularly, the present invention relates to the cultivation of anaerobic bacteria and to the cultivation of micro-aerophilic bacteria in an aerobic atmosphere.

In WO 2014/064359, it is proposed to improve and facilitate conditions of growth in an acellular culture of bacteria, the growth of which is sensitive to the oxygen content and notably bacteria which poorly tolerate high oxygen tensions and for which optimum growth of said bacterium requires an incubation atmosphere with a relatively reduced oxygen content with respect to the oxygen content of air, said bacteria being selected from among the following bacteria:

- anaerobic bacteria, including strict anaerobic bacteria, and
- micro-aerophilic bacteria of the type mentioned above.

By «micro-aerophilic atmosphere» is meant here air depleted in oxygen with a molar oxygen proportion of less than 10%, preferably 5%, still preferably less than 2.5%. For strict anaerobic bacteria, the oxygen content should be close to 0%, notably less than 0.1%, as mentioned above, the tolerance to very small amounts of oxygen being variable according to the species of anaerobic bacteria.

In WO 2014/064359, the addition of certain antioxidant compounds is proposed, i.e. ascorbic acid, glutathion and sodium hydrosulfide in an acellular culture medium which may give the possibility of:

- improving the growth of said bacteria by more rapidly obtaining bacteria in a sufficient concentration so as to be detectable after multiplication and/or by increasing the concentration of bacteria after a given cultivation period, i.e. per unit of time, and
- cultivating with at least one same growth level or even at a higher level, strict anaerobic bacteria in the presence of a greater amount of oxygen than in the absence of any antioxidant compound, i.e. in a micro-aerophilic atmosphere, notably with oxygen contents from 2 to 5%, but also oxygen contents greater than 5%, or even under aerobic conditions, i.e. in the presence of an oxygen level equivalent to the close oxygen content of ambient air i.e. about 21%, and
- cultivating with at least one same growth level, in an atmosphere containing higher oxygen tensions, said micro-aerophilic intracellular bacteria, which may be cultivated in the absence of an antioxidant compound, in a micro-aerophilic atmosphere, or even with a higher growth level as this is the case for the bacterium *Coxiella burnetii*; and
- cultivating with a higher growth rate, in a micro-aerophilic atmosphere, bacteria which may be cultivated, in the absence of an antioxidant compound in an atmosphere containing a high oxygen tension, but less than the oxygen content of the air, as this is the case for the optional intracellular bacterium *Mycobacterium tuberculosis*.

In WO 2014/064359, a method for cultivating in vitro bacteria in an acellular culture medium of bacteria, the growth of which is sensitive to the oxygen content, is therefore provided, the optimum growth of said bacteria requiring an incubation atmosphere with a relatively reduced oxygen content or even zero content with respect to the oxygen content of air, said bacteria being selected from among anaerobic bacteria and intracellular micro-aerophilic bacteria, characterized in that an antioxidant compound selected from ascorbic acid, glutathion and sodium hydrosulfide is added, and said bacterium is cultivated in said culture medium in the presence of oxygen.

In WO 2014/064359, ascorbic acid and glutathion are preferred since they are capable at specific doses of allowing cultivation at a higher oxygen level.

In WO 2014/064359, still more particularly, said antioxidant compounds, are applied at a concentration from 0.1 g/L to 2 g/L, or at a molar concentration from $10^{-6}$ M to $10^{-2}$ M.

Other antioxidant compounds such as sodium hydrosulfide (NaHS) or cysteine are less effective and require higher concentrations.

The addition of an antioxidant compound gives the possibility of tolerating growth in the presence of relatively higher oxygen content, or even in an ambient air atmosphere notably for intracellular micro-aerophilic bacteria such as *Coxiella burnetii* or *Helicobacter cinaedi* and strict anaerobic bacteria such as *Bacteroides*. And, this addition also gives the possibility for certain bacteria such as *Mycobacterium tuberculosis* which may be cultivated at higher oxygen tensions in the absence of an antioxidant compound, of improving their growth at reduced oxygen tensions in the presence of an antioxidant compound.

Under certain conditions, ascorbic acid appears to be too toxic and/or too acid with respect to certain bacteria and/or for certain culture media with strong doses. This was shown notably for *Mycobacterium tuberculosis* (4). On the other hand, glutathion is very expensive.

According to the present invention, the inventors randomly discovered that an equivalent effect on the growth of said anaerobic bacteria or sensitive to oxygen may also be obtained by adding into said culture medium uric acid (7,9-dihydro-1H-purine-2,6,8(3H)-trione or 2,6,8-trioxypurine) in the place of antioxidant compounds as described in WO 2014/064359, uric acid being applied in similar concentrations or less than those of ascorbic acid and of glutathion as described in WO 2014/064359.

Uric acid, although having under certain conditions antioxidant properties, is not conventionally used in microbiology as an antioxidant compound since under certain conditions, it exhibits on the contrary oxidant properties (5).

The inventors within the scope of research work on Kwashiorkor disease, a form of children malnutrition, discovered the importance of uric acid for the growth of anaerobic bacteria. They observe in these children a very particular microbial flora of the digestive tract in that it includes very few anaerobic bacteria on the one hand and a deficiency in uric acid on the other hand. This deficiency in uric acid stems from a diet not including any meat and few vegetables while uric acid stems from the degradation of purines which are for example found in a significant amount in meat-containing foods. In order to explain the specificity of the flora of these patients, they wanted to check whether uric acid would be sufficient for allowing cultivation under aerobic conditions of theoretically anaerobic bacteria, which led them to the discovery that small doses of uric acid normally present in the digestive tract may actually reestablish the growth of anaerobic bacteria, absent in patients deficient in uric acid.

This discovery is of particular importance and advantageous since uric acid is less acid and less toxic than ascorbic acid and much less expensive than glutathion i.e. about 1 Euro/g for uric acid, instead of 100 Euros/g for glutathion.

The present invention therefore has the object of an in vitro cultivation method in an acellular culture medium, of a bacterian selected from anaerobic bacteria and intracellular micro-aerophilic bacteria, wherein said bacterium is cultivated in said culture medium in the presence of oxygen, characterized in that uric acid at a concentration of at least 0.1 g/L is added into said culture medium.

Said bacteria are bacteria, the growth of which is sensitive to the oxygen content, the optimum growth of said bacterium requiring an incubation atmosphere with a relatively reduced oxygen content with respect to the oxygen content of air.

More particularly, uric acid is applied at a concentration of at least 0.2 g/L, preferably from 0.4 to 2 g/L, notably from 0.2 to 0.5 g/L, in order to obtain an equivalent or even greater effect on the growth of said bacteria sensitive to oxygen, in an aerobic atmosphere and at concentrations less than or equal to those of ascorbic acid and of glutathion alone or in a mixture allowing a similar effect on the growth of said bacteria under the same aerobic ambient atmospheres.

Uric acid may be applied as a mixture with ascorbic acid and/or glutathion but uric acid may be applied without any additional antioxidant compound in said culture medium.

As illustrated in the exemplary embodiments of the description detailed hereafter:
very many anaerobic and micro-aerophilic bacteria have improved growth in an aerobic atmosphere with uric acid in combination with ascorbic acid and glutathion, and
for certain bacteria, the growth results with uric acid were greater than those obtained with a mixture of ascorbic acid and of glutathion, and
certain anaerobic and micro-aerophilic bacteria have improved growth in an aerobic atmosphere with uric acid alone or in combination with ascorbic acid but no improved growth with ascorbic acid alone.

Preferably, the uric acid is applied in combination with ascorbic acid, still preferably with ascorbic acid and glutathion.

More particularly, said culture medium comprises the components which are again found in culture base media able to cultivate an anaerobic bacterium, comprising at least:
several carbon sources,
a source of phosphorus, preferably a phosphate salt,
a source of nitrogen, preferably an ammonium salt,
at least one salt of metal selected from among K, Mg, Na, Ca, preferably NaCl.

More particularly, said culture medium is an acellular medium and selected from an axenic medium consisting of chemical or biological substances defined qualitatively and quantitatively, and an acellular medium comprising an extract of milled material or lyzed material of pluricellular tissue. Preferably, said medium comprises a pH-regulating buffer substance for adjusting the pH from 7 to 7.5.

More particularly, said culture medium is a conventional acellular culture medium of a micro-aerophilic or anaerobic bacterium, preferably a medium comprising component selected from an extract of milled or lyzed material of a pluricellular tissue, an enzymatic digested material, notably an enzymatic digested material of casein, soya and/or animal tissue, a peptone, a yeast extract, a sugar such as dextrose or glucose, an NaCl salt and/or an $Na_2PO_4$ salt.

Still more particularly, said culture medium is a filtrate of said milled or lyzed material, notably of blood tissue or heart and/or lung tissue, when said bacterium is an extracellular bacterium such as so-called broth media of the heart-brain type, Columbia media with 5% of sheep blood or Schaedler medium as described hereafter. Other suitable conventional media are the *Brucella* or Wilkins-Chagren media. Such acellular culture media are well known to one skilled in the art. These media may be used with agar (solid or semi-solid) or without agar (liquid).

In particular polyvalent culture media may be used for anaerobic microorganisms, notably Schaedler medium.

Such acellular culture media whether they are liquid, solid or biphasic are well known to one skilled in the art. More particularly, said culture medium for anaerobic bacteria may be found as a liquid or solid or semi-solid, notably with gelosed or semi-gelosed medium.

More particularly, said bacterium is cultivated in an said incubation atmosphere comprising a greater oxygen molar proportion than the maximum tolerated tension in the absence of uric acid or of any antioxidant compound for a same growth level in a same culture period.

In practice, still more particularly, said bacterium is cultivated in an said incubation atmosphere comprising a molar oxygen proportion of less than or equal to 20%.

Still more particularly, said bacteria according to the present invention are cultivated in an atmosphere comprising an oxygen content of more than 5%, notably in air containing 5% of $CO_2$ (i.e. an oxygen content of less than 16%), or even in an aerobic atmosphere of ambient air.

Still more particularly, in certain cases, as explained hereafter, said intracellular micro-aerophilic bacteria is cultivated in a said micro-aerophilic incubation atmosphere comprising a molar oxygen proportion of less than 5%, preferably from 2 to 5%, still preferably 2.5%.

More particularly, uric acid is applied with an antioxidant compound preferably selected from among ascorbic acid and glutathion (γ-L-Glutamyl-L-cysteinylglycine) or even sodium hydrosulfide. Ascorbic acid and glutathion are preferred since they are capable at specific doses of allowing cultivation at a higher oxygen level. Still more particularly, said antioxidant compound is applied at a concentration of 1 mg/L to 2 g/L, preferably at least 100 mg/L.

Preferably, said antioxidant compound is ascorbic acid and/or glutathion, preferably at a concentration of at least 100 mg/L.

More particularly, said bacterium is a bacterium which may be cultivated in a said culture medium in the absence of uric acid or of said oxidizing compound under an atmosphere comprising an oxygen molar proportion less than the oxygen molar proportion in air, preferably less than 20%, and said bacterium is cultivated in the presence of said uric acid in said culture medium under an incubation atmosphere comprising an oxygen content of less than or equal to the oxygen proportion in air, preferably less than 20%, still preferably greater than 5%.

According to a first embodiment, said bacterium is an extracellular anaerobic bacterium which may be cultivated in an anaerobic atmosphere in the absence of said uric acid or said antioxidant compound, and growth of said bacterium is obtained in the presence of oxygen with a molar proportion less than or equal to the oxygen proportion in air.

Anaerobic bacteria may be strict anaerobic bacteria or optional anaerobic bacteria also-called aero-anaerobic bacteria, i.e. anaerobic bacteria which tolerate oxygen but do not need it for growth or aerobic bacteria which support the absence of oxygen for growth.

Among the strict anaerobic bacteria, more particularly let us mention bacteria belonging to the genera *Acidaminococcus, Alistipes, Anaerococcus, Anaerosalibacter, Amazonia, Atopobium, Bifidobacterium, Blautia, Bacteroides, Bamesiella, Clostridium, Collinsella, Dielma, Eggerthella, Finegoldia, Flavonifractor, Fusobacterium, Gordonibacter, Guyana, Holdemania, Odoribacter, Parabacteroides, Parvimonas, Prevotella, Peptostreptococcus, Peptoniphilus, Porphyromonas, Prevotella, Solobacterium, Tissierella, Tuncibacter, Ruminococcus* and *Veillonella*.

From among the optional anaerobic bacteria, more particularly let us mention the *bacteria belonging to the genera Actinomyces, Aerococcus, Aeromonas, Aneurinibacillus, Bacillus, Bartonella, Cedecea, Citrobacter, Corynebacterium, Derambacter, Eikenella, Enterobacter, Enterococcus, Escherichia, Eubacterium, Gardnerella, Gemella, Granulicatella, Hafnia, Haemophilus Kingella, Klebsellia, Lactobacillus, Lactococcus, Lysinibacillus, Morganella, Paenibacillus, Pasteurella, Pediococcus, Propionibacterium, Proteus, Providencia, Serratia, Raoultella, Rothia, Staphylococcus, Streptococcus* and *Weissella*.

According to this first more particular embodiment, an anaerobic extracellular bacterium is cultivated, notably a bacterium of the digestive tract in humans or animals in a so-called acellular medium in the presence of a molar oxygen proportion less than or equal to that of air and in the presence of said uric acid, preferably in an atmosphere of ambient air.

This first embodiment is illustrated in the example hereafter by the aerobic cultivation of *Bacteroides thetaiotaomicron* in the presence of uric acid.

These are strict anaerobic bacteria of the digestive tract, which normally are only cultivated under strictly anaerobic conditions. This is expressed when said bacteria is inoculated into a deoxygenated tube by the fact that a culture veil only appears in the low portion of the tube, while the upper portion remains untouched by any culture. If uric acid according to present invention at 200 µg/ml is added, the cultivation practically occurs up to the surface, or even completely up to the surface at the concentration of 500 µg/ml and even better at 1 g/l with uric acid like for a mixture of ascorbic acid at 500 µg/ml and of glutathion at 500 µg/ml. The bacterium produces in 24 h colonies after having been sown on gelose.

In another embodiment, said bacterium is an intracellular micro-aerophilic bacterium capable of being cultivated in a said acellular culture medium, under a micro-aerophilic atmosphere with a molar oxygen proportion of not more than 5%, preferably not more than 2.5% in the incubation atmosphere, in the absence of uric acid or of an antioxidant compound, and said bacterium is cultivated in the presence of uric acid in a said culture medium under a micro-aerophilic incubation atmosphere comprising a molar oxygen proportion between 2.5% and 20%, preferably between 5% and 16%, notably air optionally enriched with 5% of $CO_2$.

The present invention more particularly applies to micro-aerophilic bacteria because, inter alia of the addition of said uric acid.

From among the intracellular micro-aerophilic bacteria, mention may more particularly be made of bacteria of the genera *Coxiella, Mycobacterium, Helicobacter, Campylobacter* and *Vagococcus*.

This embodiment is illustrated by the aerobic cultivation of the bacterium *Mycobacterium tuberculosis* and *Helicobacter cinaedi* cultivated in ambient air.

Other species of micro-aerophilic bacteria, strict anaerobic bacteria and optional anaerobic bacteria mentioned in example 3 i.e. about 250 species, were tested with improved growths obtained under aerobic conditions in polyvalent culture media additived with uric acid.

Other features and advantages of the invention will become apparent in the light of the detailed description of the following exemplary embodiments.

EXAMPLE 1: CULTIVATION OF *BACTEROIDES THETAIOTAOMICRON* WITH A SCHAEDLER MEDIUM

A strain of the anaerobic bacterium *Bacteroides thetaiotaomicron* was obtained through the "culturomics" study of the inventors (2) also accessible in diverse deposit collections (CSUR P766 also deposited according to the Budapest Treaty on the deposit collection of DSMZ micro-organisms (Germany) on May 19, 2014 under the number DSM 28808, other strains are also accessible in diverse deposit collections such as the strains DSM 2079, ATCC 29148 and NCTC 10582).

For their production in a sufficient amount, *B. thetaiotaomicron* was cultivated in an anaerobic atmosphere at 37° C. in a polyvalent culture medium. The suitable Schaedler medium (Reference 42098; BioMérieux, La Balmes-les-Grottes, France) was tested also for cultivating anaerobic bacteria.

The Schaedler medium (marketed by BioMérieux, Marcy l'etoile, France) had the following composition for 1 liter:

| | |
|---|---:|
| Enzymatic digested material of casein | 5.6 g |
| Enzymatic digested material of soya cake | 1 g |
| Enzymatic digested material of animal tissues | 5 g |
| Yeast extract | 5 g |
| NaCl | 1.7 g |
| Potassium phosphate | 0.82 g |
| Dextrose | 5.82 g |
| Tris (hydroxymethyl) aminomethane | 3 g |
| Hemin | 0.01 g |
| L-cysteine | 0.4 g |

This Schaedler medium was supplemented by adding hydrocarbon compounds, i.e. 1 g/L of rice starch and 1 g/L of glucose (Sigma-Aldrich, Saint-Quentin Fallavier, France) and by the addition of uric acid and anti-oxidant compounds, i.e. supplemented by adding:

either 0.1 g/L of ascorbic acid (VWR International, Louvain, Belgium), 0.1 g/L of uric acid and 0.1 g/L of glutathion (Sigma-Aldrich, Saint-Quentin Fallavier, France), or 0.1; 0.2 or 0.3 g/L of uric acid alone as an antioxidant compound.

The addition of hydrocarbon starch and glucose compounds aimed here to produce $H_2$ for controlling the growth of the bacterium.

Resazurin is applied as an oxidation-reduction indicator at a concentration of 0.1 mg/ml for controlling the presence of oxygen (oxidized resazurin has a pink color, and becomes transparent in the absence of oxygen).

The aerobic culture in ambient air of *B. thetaiotaomicron* was carried out by inoculation of $10^5$ organisms/ml in a container incubated at 37° C. containing the culture medium supplemented with the addition of anti-oxidant compounds and carbon source compounds. The pH was adjusted to 7.5 by adding 10M KOH.

The strain was cultivated in parallel in an aerobic condition and by the inoculation of $10^5$ organisms/ml with the culture medium supplemented according to the present invention and with the Schaedler medium supplemented with the hydrocarbon compounds mentioned above but on the other hand without any anti-oxidant compounds.

The culture medium supplemented by adding 1 g/L of rice starch and 1 g/L of glucose inoculated under anaerobic conditions with $10^8$ cells/L of *B. thetaiotaomicron* was introduced as a positive control and for checking the production of $H_2$ by *B. thetaiotaomicron* in an anaerobic culture. These controls were carried out in parallel in an ambient atmosphere (aerobic condition). The non-inoculated culture medium was introduced as a negative control.

The growth of *B. thetaiotaomicron* was daily evaluated by the production of hydrogen. The measurement of hydrogen was carried out by means of a gas chromatograph GC-8A (Shimadzu, Champs-sur-Marne, France) equipped with a heat conductivity detector and a Chromosorb WAW 80/100 meshes column SP100 (Alltech, Carquefou, France). The nitrogen $N_2$ at a pressure of 100 kPa was used as a carrier gas. The detector and the temperatures of the injector were 200° C. and the temperature of the column was 150° C.

The negative controls remained negative without any growth occurring after one week of incubation indicating that the results reported here are not simply the result of a contamination by other microorganisms.

The positive controls were positive, a production of hydrogen was observed in the anaerobic culture of *B. thetaiotaomicron*. The *B. Thetaiotaomicron* culture inoculated under aerobic conditions without any antioxidant compounds remained negative and the hydrogen was not produced.

After incubation for 24 hours at 37° C. in ambient air (under aerobic conditions), a culture medium without any anti-oxidant compounds kept its pink color indicating the presence of oxygen and the culture remained negative for the tested strain. The aerobic culture medium with uric acid or said anti-oxidant compounds became transparent indicating the absence of oxygen.

The cultures de *B. thetaiotaomicron* made under aerobic conditions with uric acid or said anti-oxidant compounds all gave a positive culture for *B. thetaiotaomicron* with production of hydrogen after 24 hour incubation.

The growth results with uric acid without said antioxidant compound were equivalent to those obtained with a mixture of uric acid with ascorbic acid and of glutathion when the uric acid concentration alone was of at least 0.2 g/L and greater with 0.3 g/L of uric acid alone.

These results indicate that it is possible to cultivate in ambient air (aerobic condition) bacteria notoriously assumed as strictly anaerobic bacteria, in a suitable medium containing a suitable mixture of antioxidants and in particular with uric acid alone without any antioxidant.

The cultivation procedure is carried out on culture medium tubes of the Schaedler type with 0.2% of agar-agar (BioMérieux, Marcy l'etoile, France).

The Schaedler medium had the following composition for 1 liter:

| | |
|---|---|
| Enzymatic digested material of casein | 5.6 g |
| Enzymatic digested material of soya cake | 1 g |
| Enzymatic digested material of animal tissues | 5 g |
| Yeast extract | 5 g |
| NaCl | 1.7 g |
| Potassium phosphate | 0.82 g |
| Dextrose | 5.82 g |
| Tris (hydroxymethyl) aminomethane | 3 g |
| Hemin | 0.01 g |
| L-cysteine | 0.4 g |
| Agar (semi-solid medium) | 0.2% |

For each bacterium, 2 tubes are inoculated, a regenerated tube without any uric acid and a regenerated tube in which are added 500 μg/ml or 1 mg/ml of uric acid. In order to regenerate the tube, it is placed in a water bath at 100° C. until all the visible gas bubbles in the medium have disappeared. Next, for the tube with uric acid, the cooling of the tube at 50° C. is awaited (schematically until it is possible to hold it in the hand without burning oneself) and the suspension of uric acid is added. Homogenization is then performed by turning it over (3-4 for ensuring a good mixture). For each bacterium, an inoculum of $10^7$ bacteria/ml was inoculated over the whole height of the Schaedler tubes 0.2%, a normal and a supplemented one in uric acid. The tubes were incubated at 37° C. in a strict anaerobic oven for 24-48 hours.

Under these conditions, a usual growth of the bacteria from the bottom of the tube was observed up to 1.5 cm below the surface of the medium in the absence of uric acid as a witness of the anaerobic nature of this bacterium, and a growth up to the surface in the presence of 500 μg/ml ($28 \times 10^{-4}$M) of uric acid indicating growth in the presence of a larger oxygen tension than in the absence of uric acid.

Tests, in every point identical were conducted either with glutathion or ascorbic acid at 500 μg/ml. With uric acid alone, the growth is identical to what is observed with ascorbic acid.

Finally, in order to definitively validate the capability of this uric acid compound of allowing growth of strict anaerobic bacteria in the presence of oxygen, solid media were prepared, consisting of Columbia medium with 5% of sheep blood in which was added uric acid at 500 μg/ml or 1 mg/ml, or a mixture of glutathion at 500 μg/ml+ascorbic acid at 500 μg/ml or of ascorbic acid at 1 mg/ml. These geloses inoculated with anaerobic bacteria were incubated either in ambient air or in ambient air enriched with 5% of $CO_2$. Best growth was obtained with uric acid or ascorbic acid at 1 mg/ml equally.

These tests were conducted with a Columbia medium with 5% sheep blood having the following composition for 1 liter:

| | |
|---|---|
| Enzymatic digested material of casein | 5 g |
| Enzymatic digested material of animal tissues | 8 g |
| Peptone enriched with yeast | 10 g |
| Maize starch | 1 g |
| NaCl | 5 g |
| Agar-agar (if a gelosed medium) | 14 g |
| Sheep blood | 5% |

EXAMPLE 2: EFFECT OF URIC ACID ON THE CULTURE HELICOBACTER CINAEDI

A strain DSMZ 5359 was used, cultivated in the same Schaedler culture medium as described in Example 1 and under the same aerobic operating conditions at the same concentrations of uric acid except that the culture medium was not supplemented by adding hydrocarbon compounds, starch and glucose.

The bacterium was established in a culture within 24 h and confirmed by mass spectrometry of the Maldi tof type.

EXAMPLE 3: EFFECT OF URIC ACID ON THE GROWTH OF MYCOBACTERIUM TUBERCULOSIS

In this example, the inventors compared the growth of the mycobacterium Mycobacterium tuberculosis, an agent of human and animal tuberculosis, on three solid media, under identical temperature (37° C.) conditions and atmospheric conditions (5% $CO_2$).

The strain of the M. tuberculosis H37Rv type calibrated to $10^7$ colony forming units (CFU) and four clinical strains of M. tuberculosis calibrated to $10^5$ CFU or $10^6$ CFU were inoculated into sterile Petri dishes in a MOD4 medium described hereafter, enriched with ascorbic acid at 100 mg/L (MOD5), and in uric acid at 100 mg/L (MODE) or in uric acid at 200 mg/L (MOD7). Five dishes were sown for each condition.

The results of the detection times with the naked eye of colonies in days are shown in the table hereafter.

These results show that there is an improvement in significant growth by adding uric acid or ascorbic acid and no significant difference in the growth of M. tuberculosis between ascorbic acid and uric acid, showing the possibility of using uric acid as an antioxidant for cultivation in an aerobic atmosphere of mycobacteria, at a concentration at least equal to 100 mg/L.

| Total | MOD 5 | MOD6 | MOD7 |
|---|---|---|---|
| Average (days) | 4.625 | 3 | 4.25 |
| Standard deviation | 1.99582898 | 1.8973666 | 1.52752523 |
| $X^2$ test (Chi2) | Qobs | 27.117411729003 | |
| | P-value | 0.61709915998056 | |
| | Test parameter | 30 | |

| | MOD 5 | MOD 6 | MOD 7 |
|---|---|---|---|
| Patient 1: | | | |
| $10^7$ CFU/mL | | | |
| Average (days) | 4 | 4.25 | 3.25 |
| Standard deviation | 0.81649658 | 1.25830574 | 1.89296945 |
| Patient 2: | | | |
| $10^6$ CFU/mL | | | |
| Average (days) | 6.5 | 4.5 | 5.25 |
| Standard deviation | 1.29099445 | 1.29099445 | 0.5 |
| Patient 3: | | | |
| $10^5$ CFU/mL | | | |
| Average (days) | 2.25 | 2.75 | 4.75 |
| Standard deviation | 0.95742711 | 0.95742711 | 1.5 |
| Patient 4: | | | |
| $10^5$ CFU/mL | | | |
| Average (days) | 5.75 | 0.5 | 3.75 |
| Standard deviation | 1.5 | 0.57735027 | 1.5 |

The results give the possibility of drawing the conclusion of faster detection of the colonies in decreasing order with a detection at:

t=about on average 3 to 5 days for a MOD6 or MOD 7 medium (uric acid) or MOD 5 (ascorbic acid) equally, and t=about 8.5 to 10 days ($10^7$ cfu/mL) for MOD4.

TABLE A composition of the MOD4 Medium

| Components | Amount |
|---|---|
| Magnesium sulfate | 0.05 g/L |
| Ferric ammonium citrate | 0.04 g/L |
| Sodium citrate | 0.4 g/L |
| ammonium sulfate | 0.5 g/L |
| Monosodium glutamate | 0.5 g/L |
| Disodium phosphate | 1.5 g/L |
| Monopotassium phosphate | 1.5 g/L |
| Tween 80 | 5 g/L |
| Pyridoxine | 1.0 mg/L |
| Zinc sulfate | 1.0 mg/L |
| Copper sulfate | 1.0 mg/L |
| Biotin | 0.5 mg/L |
| Calcium chloride | 0.5 mg/L |
| OADC | 100.0 ml/L |
| Glycerol | 5.0 ml/L |
| Sheep blood | 50 ml/L |
| De-complemented fetal calf serum | 150 ml/L |
| Egg lecithin | 5 g/L |
| Yeast extract | 1.0 g/L |
| Digested material of pancreatic casein | 1.0 g/L |
| Glucose | 2.0 g/L |
| Bovine serum albumin | 1.65 g/L |
| Nicotinamide Adenine Dinucleotide (NAD) | 22 g/L |
| Vinylpyrrolidine Copolymer | 2 ml/L |
| Citric acid | 101 mg/L |
| Hemin | 330 μg/L |
| Agar-agar | 13 g/L |

EXAMPLE 4: EFFECT OF URIC ACID IN A SHAEDLER SOLID MEDIUM ON THE GROWTH OF A PANEL OF BACTERIA

1) The following anaerobic and micro-aerophilic bacteria were cultivated under aerobic conditions (under an atmosphere of ambient air) at 37° C. with improved growths in a solid culture medium consisting in a Schaedler medium with 0.2% agar-agar (Sigma-Aldrich, Saint-Quentin Fallavier, France) described in Example 1 supplemented with 1 g/L ascorbic acid (VWR, Louvain, Belgium)+100 mg/L of glutathion (Sigma, Quentin Fallavier, France)+400 mg/L of uric acid (Sigma, Quentin Fallavier, France).

The pH was adjusted to 7.5 with 10M KOH before passing into the autoclave. The antioxidant compounds were dissolved in 10 mL of distilled water, filtered with a microfilter of 0.2 μm and then added into the autoclaved medium at 50° C. so as to be sterilized before being cooled in solid form into gelose.

In the tables hereafter, the growth times correspond to the appearance of the first colonies visible to the naked eye.

TABLE 1A strict anaerobic bacteria (82 species and 145 strains).

| Phylum | Genus | species | Number of tested strains | Growth Time |
|---|---|---|---|---|
| Actinobacteria | Bifidobacterium | Bifidobacterium adolescentis | 1 | 72 H |
| | | Bifidobacterium brevis | 1 | 72 H |
| | | Bifidobacterium catenulatum | 1 | 72 H |
| | | Bifidobacterium longum | 1 | 72 H |
| | | Bifidobacterium pseudocatenulatum | 1 | 72 H |
| | Collinsella | Collinsella aerofaciens | 1 | 96 H |
| | | Collinsella massilioamazoniensis | 2 | 72 H |
| | | Collinsella tanakaei | 2 | 96 H |
| | Eggerthella | Eggerthella lenta | 2 | 48 H |
| | Gordonibacter | Gordonibacter pamelaeae | 1 | 72 H |
| Bacteroidetes | Alistipes | Alistipes finegoldii | 2 | 96 H |
| | | Alistipes indistinctus | 4 | 96 H |
| | | Alistipes putredinis | 1 | 96 H |
| | | Alistipes shahii | 2 | 96 H |
| | Bacteroides | Bacteroides caccae | 6 | 72 H |
| | | Bacteroides fragilis | 2 | 48 H |
| | | Bacteroides intestnalis | 5 | 48 H |
| | | Bacteroides nordii | 1 | 48 H |
| | | Bacteroides ovatus | 3 | 48 H |
| | | Bacteroides stercoris | 1 | 48 H |
| | | Bacteroides thetaiotaomicron | 1 | 48 H |
| | | Bacteroides timonensis | 1 | 72 H |
| | | Bacteroides uniformis | 1 | 48 H |
| | | Bacteroides vulgatus | 1 | 48 H |
| | Barnesiella | Barnesiella intestinihominis | 2 | 48 H |
| | Odoribacter | Odoribacter splanchnicus | 1 | 48 H |
| | Parabacteroides | Parabacteroides distasonis | 1 | 48 H |
| | | Parabacteroides johnsonii | 1 | 48 H |
| | | Parabacteroides merdae | 1 | 48 H |
| | Porphyromonas | Porphyromonas asaccharolityca | 1 | 72 H |
| | Prevotella | Prevotella buccalis | 1 | 72 H |
| Firmicutes | Acidaminococcus | Acidaminococcus intestini | 2 | 48 H |
| | Amazonia | Amazonia massiliensis | 1 | 48 H |
| | Anaerococcus | Anaerococcus vaginalis | 7 | 72 H |
| | Anaerosalibacter | Anaerosalibacter bizertensis | 2 | 72 H |
| | | Anaerosalibacter massiliensis | 3 | 72 H |
| | Blautia | Blautia coccoides | 1 | 96 H |
| | Clostridium | Clostridium amazonitimonense | 1 | 72 H |
| | | Clostridium amylolyticum | 1 | 72 H |
| | | Clostridium anorexicamassiliensis | 2 | 72 H |
| | | Clostridium anorexicus | 3 | 72 H |
| | | Clostridium baratii | 1 | 72 H |
| | | Clostridium bartlettii | 1 | 72 H |
| | | Clostridium bifermentans | 1 | 72 H |
| | | Clostridium bolteae | 1 | 72 H |
| | | Clostridium butyricum | 4 | 72 H |
| | | Clostridium clostridioforme | 2 | 72 H |
| | | Clostridium cochlearium | 1 | 72 H |
| | | Clostridium dakarense | 1 | 72 H |
| | | Clostridium difficile | 1 | 96 H |
| | | Clostridium glycolicum | 3 | 72 H |
| | | Clostridium hathewayi | 3 | 48 H |
| | | Clostridium jeddahense | 2 | 72 H |
| | | Clostridium lituseburense | 1 | 72 H |
| | | Clostridium paraputrificum | 3 | 72 H |
| | | Clostridium perfringens | 2 | 72 H |
| | | Clostridium ramosum | 1 | 72 H |
| | | Clostridium rubiinfantis | 1 | 72 H |
| | | Clostridium sartagoforme | 1 | 72 H |
| | | Clostridium senegalense | 4 | 72 H |
| | | Clostridium sordellii | 4 | 48 H |
| | | Clostridium sporogenes | 3 | 72 H |
| | | Clostridium subterminale | 3 | 72 H |
| | | Clostridium symbiosum | 1 | 72 H |
| | | Clostridium tertium | 2 | 48 H |
| | Dielma | Dielma fastidiosa | 1 | 48 H |
| | Finegoldia | Finegoldia magna | 1 | 48 H |
| | Flavonifractor | Flavonifractor plautii | 2 | 48 H |
| | Guyana | Guyana massiliensis | 1 | 72 H |
| | Holdemania | Holdemania massiliensis | 1 | 72 H |

TABLE 1A-continued strict anaerobic bacteria (82 species and 145 strains).

| Phylum | Genus | species | Number of tested strains | Growth Time |
|---|---|---|---|---|
| | Parvimonas | Parvimonas micra | 1 | 72 H |
| | Peptoniphilus | Peptoniphilus asaccharolyticus | 3 | 72 H |
| | | Peptoniphilus harei | 1 | 72 H |
| | | Peptoniphilus senegalensis | 2 | 72 H |
| | Peptostreptococcus | Peptostreptococcus asaccharolyticus | 1 | 72 H |
| | Ruminococcus | Ruminococcus gnavus | 1 | 48 H |
| | Tissierella | Tissierella praeacuta | 1 | 72 H |
| | Turicibacter | Turicibacter sanguinis | 1 | 72 H |
| | Veillonella | Veillonella dispar | 2 | 48 H |
| | | Veillonella parvula | 1 | 48 H |
| Fusobacteria | Fusobacterium | Fusobacterium necrophorum | 2 | 48 H |
| | | Fusobacterium nucleatum | 1 | 48 H |

TABLE 1B micro-aerophilic bacteria (7 species, 7 tested strains)

| Phylum | Genera | species | Number of strains | Growth time |
|---|---|---|---|---|
| Actinobacteria | Mycobacterium | Mycobacterium smegmatis | 1 | 96 H |
| Proteobacteria | Campylobacter | Campylobacter coli | 1 | 48 H |
| | | Campylobacter concisus | 1 | 48 H |
| | | Campylobacter cuniculorum | 1 | 48 H |
| | | Campylobacter fetus | 1 | 48 H |
| | | Campylobacter jejuni | 1 | 48 H |
| Firmicutes | Vagococcus | Vagococcus fluvialis | 1 | 48 H |

TABLE 1C optional anaerobic bacteria (154 species, 421 strains)

| Phylum | Genera | species | Number of strains | Growth time |
|---|---|---|---|---|
| Actinobacteria | Actinomyces | Actinomyces neuii | 2 | 48 H |
| | | Actinomyces oris | 4 | 48 H |
| | | Actinomyces radingae | 1 | 48 H |
| | | Actinomyces urogenitalis | 1 | 48 H |
| | Corynebacterium | Corynebacterium accolens | 2 | 48 H |
| | | Corynebacterium afermentans | 5 | 48 H |
| | | Corynebacterium amycolatum | 3 | 48 H |
| | | Corynebacterium aurimucosum | 1 | 48 H |
| | | Corynebacterium efficiens | 1 | 48 H |
| | | Corynebacterium jeikeium | 2 | 48 H |
| | | Corynebacterium minutissimum | 1 | 48 H |
| | | Corynebacterium propinquum | 1 | 48 H |
| | | Corynebacterium pseudodiphtheriticum | 4 | 48 H |
| | | Corynebacterium simulans | 2 | 48 H |
| | | Corynebacterium striatum | 2 | 48 H |
| | | Corynebacterium suicordis | 1 | 48 H |
| | | Corynebacterium urealyticum | 2 | 48 H |
| | | Corynebacterium ihumii | 1 | 48 H |
| | | Corynebacterium tuberculostearicum | 3 | 48 H |
| | | Corynebacterium ureicelerivorans | 1 | 48 H |
| | Dermabacter | Dermabacter hominis | 2 | 48 H |
| | Gardnerella | Gardnerella vaginalis | 2 | 24 H |
| | Propionibacterium | Propionibacterium acnes | 4 | 24 H |
| | | Propionibacterium avidum | 2 | 24 H |
| | Rothia | Rothia aeria | 1 | 48 H |
| | | Rothia dentocariosa | 2 | 24 H |
| Firmicutes | Aerococcus | Aerococcus urinae | 2 | 48 H |
| | | Aerococcus viridans | 2 | 48 H |
| | Aneurinibacillus | Aneurinibacillus migulanus | 1 | 24 H |
| | Bacillus | Bacillus amyloliquefaciens | 2 | 36 H |
| | | Bacillus aquimaris | 1 | 48 H |
| | | Bacillus arsenicus | 1 | 24 H |
| | | Bacillus badius | 1 | 24 H |
| | | Bacillus bataviensis | 1 | 24 H |

TABLE 1C-continued optional anaerobic bacteria (154 species, 421 strains)

| Phylum | Genera | species | Number of strains | Growth time |
|---|---|---|---|---|
| | | Bacillus cereus | 7 | 24 H |
| | | Bacillus circulans | 3 | 24 H |
| | | Bacillus clausii | 1 | 24 H |
| | | Bacillus coagulans | 1 | 24 H |
| | | Bacillus firmus | 2 | 24 H |
| | | Bacillus flexus | 4 | 24 H |
| | | Bacillus koreensis | 1 | 24 H |
| | | Bacillus lentus | 1 | 24 H |
| | | Bacillus liqueniformis | 4 | 24 H |
| | | Bacillus massilioamazoniensis | 1 | 24 H |
| | | Bacillus megaterium | 1 | 24 H |
| | | Bacillus oleronius | 1 | 24 H |
| | | Bacillus pumilus | 3 | 24 H |
| | | Bacillus rubiinfantis | 1 | 24 H |
| | | Bacillus siralis | 4 | 24 H |
| | | Bacillus subtilis | 6 | 24 H |
| | | Bacillus thermoamylovorans | 3 | 24 H |
| | | Bacillus vallismortis | 1 | 24 H |
| | Enterococcous | Enterococcus avium | 9 | 24 H |
| | | Enterococcus casseliflavus | 3 | 24 H |
| | | Enterococcus cecorum | 1 | 24 H |
| | | Enterococcus dispar | 2 | 24 H |
| | | Enterococcus durans | 9 | 24 H |
| | | Enterococcus faecalis | 13 | 24 H |
| | | Enterococcus faecium | 10 | 24 H |
| | | Enterococcus gallinarum | 10 | 24 H |
| | | Enterococcus hirae | 8 | 24 H |
| | | Enterococcus malodoratus | 2 | 24 H |
| | | Enterococcus phoeniculicola | 1 | 24 H |
| | | Enterococcus pseudoavium | 1 | 24 H |
| | | Enterococcus raffinosus | 1 | 24 H |
| | Eubacterium | Eubacterium limosum | 2 | 24 H |
| | | Eubacterium tenue | 3 | 24 H |
| | Gemella | Gemella morbillorum | 2 | 24 H |
| | Granulicatella | Granulicatella elegans | 1 | 72 H |
| | Lactobacillus | Lactobacillus agilis | 3 | 24 H |
| | | Lactobacillus fermentum | 3 | 24 H |
| | | Lactobacillus gasseri | 2 | 24 H |
| | | Lactobacillus johnsonii | 1 | 24 H |
| | | Lactobacillus kalixensis | 1 | 24 H |
| | | Lactobacillus mucosae | 2 | 24 H |
| | | Lactobacillus paracasei | 2 | 24 H |
| | | Lactobacillus plantarum | 2 | 24 H |
| | | Lactobacillus reuteri | 3 | 24 H |
| | | Lactobacillus sakei | 4 | 24 H |
| | Lactococcus | Lactococcus garvieae | 1 | 24 H |
| | | Lactococcus lactis | 1 | 24 H |
| | Lysinibacillus | Lysinibacillus boronitolerans | 2 | 24 H |
| | | Lysinibacillus fusiformis | 1 | 24 H |
| | | Lysinibacillus meyeri | 1 | 24 H |
| | | Lysinibacillus sphaericus | 2 | 24 H |
| | Paenibacillus | Paenibacillus lactis | 2 | 48 H |
| | Pediococcus | Pediococcus acidilactici | 1 | 48 H |
| | | Pediococcus pentosaceus | 2 | 48 H |
| | Staphylococcus | Staphylococcus aureus | 4 | 24 H |
| | | Staphylococcus capitis | 6 | 24 H |
| | | Staphylococcus caprae | 4 | 24 H |
| | | Staphylococcus cohnii | 7 | 24 H |
| | | Staphylococcus epidermidis | 2 | 24 H |
| | | Staphylococcus faecalis | 2 | 24 H |
| | | Staphylococcus haemolyticus | 6 | 24 H |
| | | Staphylococcus hominis | 3 | 24 H |
| | | Staphylococcus intermedius | 3 | 24 H |
| | | Staphylococcus lugdunensis | 6 | 24 H |
| | | Staphylococcus pasteuri | 3 | 24 H |
| | | Staphylococcus pettenkoferi | 2 | 24 H |
| | | Staphylococcus saprophyticus | 3 | 24 H |
| | | Staphylococcus schleiferi | 2 | 24 H |
| | | Staphylococcus simulans | 5 | 24 H |
| | | Staphylococcus warneri | 4 | 24 H |
| | Streptococcus | Streptococcus agalactiae | 3 | 24 H |
| | | Streptococcus anginosus | 4 | 24 H |
| | | Streptococcus constellatus | 2 | 24 H |
| | | Streptococcus cristatus | 3 | 24 H |
| | | Streptococcus dysgalactiae | 5 | 24 H |

TABLE 1C-continued optional anaerobic bacteria (154 species, 421 strains)

| Phylum | Genera | species | Number of strains | Growth time |
|---|---|---|---|---|
| | | *Streptococcus equinus* | 4 | 24 H |
| | | *Streptococcus gallolyticus* | 2 | 24 H |
| | | *Streptococcus gordonii* | 2 | 24 H |
| | | *Streptococcus intermedius* | 3 | 24 H |
| | | *Streptococcus lutetiensis* | 7 | 24 H |
| | | *Streptococcus mitis* | 5 | 24 H |
| | | *Streptococcus oralis* | 5 | 24 H |
| | | *Streptococcus parasanguinis* | 4 | 24 H |
| | | *Streptococcus pneumonias* | 3 | 24 H |
| | | *Streptococcus pyogenes* | 1 | 24 H |
| | | *Streptococcus salivarius* | 3 | 24 H |
| | | *Streptococcus sanguinis* | 2 | 48 H |
| | *Weissella* | *Weissella cibaria* | 2 | 48 H |
| Proteobacteria | *Aeromonas* | *Aeromonas urinae* | 2 | 48 H |
| | | *Aeromonas hydrophila* | 1 | 48 H |
| | *Bartonella* | *Bartonella henselae** | 1 | 120 H |
| | *Cedecea* | *Cedecea lapagei* | 1 | 24 H |
| | | *Cedecea neteri* | 1 | 24 H |
| | *Citrobacter* | *Citrobacter braakii* | 4 | 24 H |
| | | *Citrobacter freundii* | 2 | 24 H |
| | | *Citrobacter koseri* | 3 | 24 H |
| | | *Citrobacter sedlakii* | 1 | 24 H |
| | *Enterobacter* | *Enterobacter aerogenes* | 4 | 24 H |
| | | *Enterobacter asburiae* | 2 | 24 H |
| | | *Enterobacter cloacae* | 5 | 24 H |
| | | *Enterobacter kobei* | 2 | 24 H |
| | *Eikenella* | *Eikenella corrodens* | 1 | 48 H |
| | *Escherichia* | *Escherichia coli* | 10 | 24 H |
| | *Hafnia* | *Hafnia alvei* | 2 | 48 H |
| | *Haemophilus* | *Haemophilus influenzae** | 3 | 48 H |
| | | *Haemophilus parainfluenzae** | 3 | 48 H |
| | *Kingella* | *Kingella kingae* | 1 | 24 H |
| | *Klebsiella* | *Klebsiella oxytoca* | 2 | 24 H |
| | | *Klebsiella pneumoniae* | 3 | 24 H |
| | *Morganella* | *Morganella morganii* | 2 | 48 H |
| | *Pasteurella* | *Pasteurella multocida* | 3 | 48 H |
| | *Proteus* | *Proteus mirabilis* | 2 | 24 H |
| | | *Proteus vulgaris* | 3 | 24 H |
| | *Providencia* | *Providencia heimbachae* | 1 | 24 H |
| | | *Providencia rettgeri* | 2 | 24 H |
| | | *Providencia stuartii* | 2 | 24 H |
| | *Serratia* | *Serratia liquefaciens* | 2 | 24 H |
| | | *Serratia marcescens* | 3 | 24 H |
| | | *Serratia ureilytica* | 1 | 24 H |
| | *Raoultella* | *Raoultella ornithinolytica* | 1 | 48 H |

2) 13 anaerobic bacteria and 1 micro-aerophilic bacteria (*Campylobacter*) were tested comparatively cultivated under aerobic conditions (under an atmosphere of ambient air) at 37° C. with improved growths in a sodium culture medium consisting in a Schaedler medium with 0.2% of agar-agar not supplemented or supplemented with:
  i.e. 1 g/L of ascorbic acid,
  i.e. 400 mg/L of uric acid, and
  i.e. 1 g/L of ascorbic acid+400 mg/L of uric acid.

The tested bacteria were: *Bacteroides ovatus, Clostidium massilioamazoniensis; Anaerosalibacter bizertensis, Clostrididum paraperfringens, Clostridium sporogenes, Peptomphllus harei, Anegoldia magna, Tuncibacter sanguinis, Propionibacterium acnes, Bacteroides timonensis, Eikenella corrodens, Clostridium glycolicum, Bifidobacterium brevis, Campylobacter ureolyticus.*

The results reported in table 2 show that 5 bacteria i.e. about ⅓ of the bacteria only have improved growth with uric acid (AU) alone or in combination with ascorbic acid (AA) and not with ascorbic acid alone.

In Table 2:—« o » means: no colony was detected with the naked eye at t=96 h, and—"positive" means: colonies detected with the naked eye at t=96 h.

TABLE 2

| | Schaedler medium alone | Schaedler medium + AA | Schaedler medium + UA | Schaedler medium + AA + UA |
|---|---|---|---|---|
| *Peptoniphilus harei* | 0 | 0 | 0 | Positive |
| *Finegoldia magna* | 0 | 0 | 0 | Positive |
| *Clostridium glycolicum* | 0 | 0 | Positive | Positive |
| *Bifidobacterium brevis* | 0 | 0 | Positive | Positive |
| *Campylobacter ureolyticus* | 0 | 0 | 0 | Positive |

EXAMPLE 5: EFFECT OF URIC ACID IN A LIQUID HEMOCULTURE MEDIUM ON THE GROWTH OF ANAEROBIC BACTERIA

Hemocultures of strict anaerobic bacteria were made, inoculated to $10^5$ cfu/mL on a culture medium: BD BACTEC™ Plus Aerobic/F. comprising 25 ml of enriched Trypticase soya broth, with resines (Reference: 442192) at 37° C. in an aerobic atmosphere with uric acid a 400 mg/L and without uric acid and in an anaerobic atmosphere without uric acid. The detection of the growth was ensured by detection of the production of $CO_2$ with the BD BACTEC™ 9000 Series Instrumented Blood Culture Systems device.

The comparative growth results reported in Table B hereafter establish that the growth detection was slightly faster in an aerobic atmosphere with uric acid (« UA » in Table B) at 400 mg/L than in an anaerobic atmosphere and considerably faster than under aerobic conditions without uric acid.

TABLE B

| | | Growth time | Growth time | Growth time | Averages | Standard deviation |
|---|---|---|---|---|---|---|
| *Clostridium tertium* | Aerobic with UA | 4 h | 5 h | 4 h | 4.33333333 | 0.57735027 |
| *Clostridium tertium* | Aerobic without UA | 96 h | 96 h | 96 h | 96 | 0 |
| *Clostridium tertium* | Anaerobic without UA | 6 h | 4 h | 6 h | 5.33333333 | 1.15470054 |
| *Clostridium perfringens* | Aerobic with UA | 7 h | 5 h | 6 h | 6 | 1 |
| *Clostridium perfringens* | Aerobic without UA | 96 h | 96 h | 96 h | 96 | 0 |
| *Clostridium perfringens* | Anaerobic without UA | 5.5 h | 4 h | 4.5 h | 4.66666667 | 0.76376262 |
| *Clostridium butirycum* | Aerobic with UA | 8 h | 6 h | 6 h | 6.66666667 | 1.15470054 |
| *Clostridium butirycum* | Aerobic without AU | 96 h | 96 h | 96 h | 96 | 0 |
| *Clostridium butirycum* | Anaerobic without AU | 4 h | 6 h | 5 h | 5 | 1 |

BIBLIOGRAPHIC REFERENCES

[1] La Scola B, Fournier P E, Raoult D. Burden of emerging anaerobes in the MALDI-TOF and 16S rRNA gene sequencing era. Anaerobe 2011; 17:106-112

[2] Lagier J C et al., Microbial culturomics: paradigm shift in the human gut microbiome study. Clin Microbiol Infect. 2012; 18:1185-93) [11] D. A. Podkopaeva et al. O: idative stress and antioxidant cell protection systems in the micro-aerophilic bacterium *Spirillum winogradskii*. Microbiology, Vol. 72, no. 5, 2003, pages 534-541.

[3] Omsland A, Cockrell D C, Howe D, et al. Host cell-free growth of 3he Q fever bacterium *Coxiella burnetii*. Proc. Natl. Acad. Sci. U.S.A. 2009; 106:4430-4434.

[4] Vilchéze Catherine, Travis Hartman, Brian Weinrick, and William R. Jacobs Jr*in Nat Commun. 2013; 4: 1881. doi:10.1038/ncomms2898

[5] Yuri Y. Sautin and Richard J. Johnson in Nucleosides Nucleotides Nucleic Acids. June 2008; 27(6): 608-619.uric acid:oxidant-antioxydant paradox.

The invention claimed is:

1. A method for cultivating, in vitro, in an acellular culture medium, a strict anaerobic bacterium, wherein said strict anaerobic bacterium is cultivated in said acellular culture medium under an atmosphere comprising oxygen gas, and wherein uric acid at a concentration of at least 0.1 g/L is added to said acellular culture medium.

2. The method according to claim 1, wherein the uric acid is added at a concentration of at least 0.2 g/L.

3. The method according to claim 1, wherein the uric acid is added without any additional antioxidant compound in said acellular culture medium.

4. The method according to claim 1, wherein the uric acid is added with at least one additional antioxidant compound in said culture medium.

5. The method according to claim 4, wherein the uric acid is added in combination with at least one additional antioxidant compound selected from the group consisting of ascorbic acid and glutathion.

6. The method according to claim 4, wherein the uric acid is added in combination with ascorbic acid and glutathion.

7. The method according to claim 1, wherein said acellular medium is selected from the group consisting of:

an axenic medium consisting of chemical or biological substances qualitatively and quantitatively defined, and a medium comprising an extract of milled or lysed material of pluricellular tissue.

8. The method according to claim 1, wherein said strict anaerobic bacterium is an extracellular strict anaerobic bacterium, and wherein said culture medium comprises a member selected from the group consisting of an extract of milled or lysed material of pluricellular tissue, an enzymatic digested material of casein, soya, and/or animal tissue, a peptone, a yeast extract, a sugar, a salt NaCl, $Na_2PO_4$, and a combination thereof.

9. The method according to claim 1, wherein said strict anaerobic bacterium is cultivated under an atmosphere of ambient air.

* * * * *